United States Patent
Feehery et al.

(10) Patent No.: US 8,980,553 B2
(45) Date of Patent: Mar. 17, 2015

(54) METHODS AND COMPOSITIONS FOR ENRICHING EITHER TARGET POLYNUCLEOTIDES OR NON-TARGET POLYNUCLEOTIDES FROM A MIXTURE OF TARGET AND NON-TARGET POLYNUCLEOTIDES

(75) Inventors: George R. Feehery, West Newbury, MA (US); Fiona Stewart, Ipswich, MA (US); James McFarland, Beverly, MA (US); Sriharsa Pradhan, Wenham, MA (US)

(73) Assignee: New England Biolabs, Inc., Ipswitch, MA (US)

( * ) Notice: Subject to any disclaimer, the term of this patent is extended or adjusted under 35 U.S.C. 154(b) by 335 days.

(21) Appl. No.: 13/435,590

(22) Filed: Mar. 30, 2012

(65) Prior Publication Data

US 2012/0252009 A1 Oct. 4, 2012

Related U.S. Application Data

(60) Provisional application No. 61/471,134, filed on Apr. 2, 2011, provisional application No. 61/537,761, filed on Sep. 22, 2011, provisional application No. 61/598,715, filed on Feb. 14, 2012, provisional application No. 61/599,253, filed on Feb. 15, 2012.

(51) Int. Cl.
*C12Q 1/68* (2006.01)
*C07H 21/00* (2006.01)

(52) U.S. Cl.
CPC ................................ *C12Q 1/6806* (2013.01)
USPC ............................................ 435/6.1; 536/25.4

(58) Field of Classification Search
CPC ........ C12Q 1/68; C12Q 1/6834; C12N 15/00; C12N 15/1006
USPC ................... 435/6.1, 6.12; 536/25.4
See application file for complete search history.

(56) References Cited

U.S. PATENT DOCUMENTS

| | | | |
|---|---|---|---|
| 7,670,773 B2 | 3/2010 | Minassian et al. | |
| 7,785,772 B2* | 8/2010 | Ahlquist et al. | 435/4 |
| 7,906,288 B2* | 3/2011 | Nelson et al. | 435/6.12 |
| 8,062,854 B2* | 11/2011 | Schmidt et al. | 435/7.21 |
| 2004/0259096 A1* | 12/2004 | Allen et al. | 435/6 |
| 2005/0196390 A1* | 9/2005 | Langley et al. | 424/94.1 |
| 2008/0075755 A1* | 3/2008 | Deschatelets et al. | 424/427 |
| 2008/0220433 A1* | 9/2008 | Ahlquist et al. | 435/6 |
| 2008/0260743 A1* | 10/2008 | Rehli | 424/139.1 |
| 2009/0123914 A1* | 5/2009 | Erikson et al. | 435/6 |

OTHER PUBLICATIONS

Cross et al., Purification of CpG islands using a methylated DNA binding column. Nature Genetics 6 :236 (1994) http://www.nature.coming/journal/v6/n3/pdf/ng0394-236.pdf.*
Asakawa et al. Human BAC library: construction and rapid screening. Gene 191: 69 (1997).*
Bird, A. Horizon Symposium held May 5-7, 2005—Abstract Only.*
DNA Methylation http://en.wikipedia.org/wiki/DNA_methylation.*
Ehrlich et al. Amount and distribution of 5-methylcytosine in human DNA from different types of tissues or cells. Nucleic Acids Research 10 (8) : 2709 (1982).*
Grosveld et al. The construction of cosmid libraries which can be used to transform eukaryotic cells. Nucleic Acids Research 10 (21) :6715 (1982).*
Jabbari et al. Evolutionary changes in CpG and methylation levels in the genome of vertebrates. Gene 205 : 109 (1997).*
Jabbari et al. Cytosine methylation and CpG, TpG (CpA) and TpA frequencies. Gene 333 : 143 (2004).*
Laird et al.Principles and challenges of genome-wide DNA methylation analysis. Nature Reviews, Genetics 11 :101 (2010).*
Law et al., Establishing, maintaining and modifying DNA methylation patterns in plants and animals. Nature Reviews, Genetics 11 (3) : 204 (2010).*
Nass, M. Differential methylation of mitochondrial and nuclear DNA in cultured mouse, hamster and virus-transformed hamster cells in vivo and in vitro methylation. J. of Molecular Biology 80 : 155 (1973).*
Pollack et al. Methylation pattern of mouse mitochondrial DNA. Nucleic Acids Research 12 (12) : 4811 (1984).*
Shimizu et al. CpG distribution patterns in methylated and non-methylated species. Gene 205 :103 (1997).*
Shmookler et al. Mitochondrial DNA in Mortal and Immortal Human Cells J. of Biological Chemistry 258 (15) :9078 (1983).*
Shock et al. DNA methyltransferase 1, cytosine methylation, and cytosine hydroxymethylation in mammalian mitochondria. PNAS108 (9) : 3630 (2011).*
Tucker, K. Minireview : Methylated Cytosine and the Brain : A new base for Neuroscience. Neuron 30 :649 (2001).*
Wu, et al. Lab Chip, 9:1193-1199 (2009).
Horz, et al., Anaerobe 16:47-53 (2010).
Dewhirst et al. J. Bacterol, 192(19):5002-17 (2010).
Voo, et al., Mol Cell Biol. 20(6): 2108-2121 (2000).
Pradhan, S. et al., J. Biol. Chem., 274, 33002-33010 (1999).
Qian, J. Biol. Chem. 283: 34490-34494 (2008).
Sambrook et al., Molecular Cloning: A Laboratory Manual, 3rd ed. pp. 6.4-6.11, Cold Spring Harbor Lab Press, Cold Spring Harbor, NY, 2001.

* cited by examiner

*Primary Examiner* — Ethan C Whisenant
(74) *Attorney, Agent, or Firm* — New England Biolabs, Inc; Harriet M. Strimpel (57) ABSTRACT

Compositions and methods are provided for enriching non-target polynucleotides from a mixture of non-target and target polynucleotides where differences between the target polynucleotides and the non-target polynucleotides include the extent of modified bases that are present in a greater density in the target polynucleotides than in the non-target polynucleotides. This permits the target polynucleotides to be selectively and rapidly bound to an affinity matrix such as affinity protein-coated magnetic beads providing enrichment of the non-target polynucleotides in the supernatant. One use of this enrichment is to remove human genomic DNA from a mixture of DNAs obtained from human tissue samples to enrich for polynucleotides in a microbiome so as to characterize the microbiome by DNA sequencing.

20 Claims, 8 Drawing Sheets

METHODS AND COMPOSITIONS FOR ENRICHING EITHER TARGET POLYNUCLEOTIDES OR NON-TARGET POLYNUCLEOTIDES FROM A MIXTURE OF TARGET AND NON-TARGET POLYNUCLEOTIDES

BACKGROUND

Viruses, bacterial, yeast and eukaryotic multicellular organisms may coexist in complex associations in nature. An example of this type of association is that of microbiomes, which inhabit mammalian hosts. Rapid DNA sequencing techniques have been used to investigate microbiomes. The accuracy of the species identification has been adversely affected by uncertainty concerning the presence and amount of mammalian genomic DNA in the samples that affect the signal to noise ratio. This is particularly problematic in those situations where the DNA of interest is present in very small amounts amidst a high background of host genomic material.

Zhigang Wu, et al. (*Lab Chip*, 9:1193-1199 (2009)) developed a microfluidic device to physically separate bacterial cells from human blood cells based on soft inertial force-induced migration using flow-defined, curved and focused sample flow inside a microfluidic device resulting in 300-fold enrichment of bacteria. This type of cell separation can only reduce background contamination of the DNA between two types of cells if the cells are viable.

Another method used to isolate DNA from sepsis-causative bacteria in blood relies on the selective lysis of human-nucleated cells using a chaotropic reagent (MolYsis, Molzym GmbH, Bremen, Germany). This method also relies on viable cells. A salt-resistant DNase was used to degrade human DNA from lyzed cells, while intact bacterial cells were unaffected by DNAse. The DNAse was then inactivated and the bacterial DNA extracted and purified for analysis. The technique reduces the total human DNA concentration in the sample by 99.5%. However, total bacterial DNA recovery was low at only 30% of the expected total (Horz, et al., *Anaerobe* 16:47-53 (2010)).

At present, there is no satisfactory method for enriching target DNA from an environmental sample, which contains a mixture of DNAs under conditions in which loss of target DNA is minimized and viable cells as a source of DNA are not a requirement.

SUMMARY

In an embodiment of the invention, a composition is provided that includes a mixture of non-target polynucleotides and target polynucleotides, each of a size in the range of 10-100 kb. The composition also includes a matrix coated with a protein or polypeptide domain to form an affinity matrix. Examples of the affinity matrix include a methyl-binding domain (MBD) selected from the group consisting of UHRF1(SRA), CXX1, DNMT1, MBD or methyl-binding variants thereof. These methyl-binding proteins may be attached to the matrix by means of an Fc portion fused to MBD which binds to protein A coated on the matrix. Examples of the matrix include magnetic beads.

The affinity matrix selectively binds the target polynucleotides containing modified bases where for example the bases are methylated cytosines. The modified bases may occur at a frequency of at least 1 modified base in 200 bases. The composition further includes a buffer containing effective amounts of a salt such as 10 mM-800 mM and a non-ionic detergent.

In an embodiment of the invention, a method is provided for enriching polynucleotides from a mixture that includes: (a) obtaining a composition as described above; (b) permitting binding of the target polynucleotides to the affinity matrix; and (c) obtaining an enriched preparation of non-target polynucleotides in a supernatant fraction.

In a further embodiment of the above method, the non-target polynucleotides in the supernatant consist of at least 90% of the non-target polynucleotides in the mixture prior to enrichment and/or the target polynucleotides in the supernatant consist of no more than 10% of the target polynucleotides in the mixture prior to enrichment.

In a further embodiment of the above method, the mixture of polynucleotides prior to enrichment is obtained from a biological sample and comprises prokaryotic and mammalian genomic DNA wherein the mixture comprises at least 50% mammalian genomic DNA.

In a further embodiment of the above method, the non-target polynucleotides in the supernatant are analyzed by sequencing, cloning or amplification to determine a genomic identity for the non-target polynucleotides.

In a further embodiment of the invention, a method is provided for enhancing separation of polynucleotides containing methylated cytosine adjacent to a guanine (CpG) from unmethylated polynucleotides that includes: providing a composition described above wherein the modified bases are methylated CpGs; permitting the CpG-methylated polynucleotides to bind to the affinity matrix to form a product that is immobilized on the matrix; and performing amplification and/or sequencing of at least one of the bound polynucleotides or the unbound polynucleotides.

In addition, the mixture of methylated and unmethylated polynucleotides may include fragments from one or more bacterial genomes and one or more mammalian genomes.

In another embodiment of the invention, a composition is provided that includes: a target DNA containing methylated CpG, the target DNA being capable of binding to MBD beads; a non-target DNA that cannot readily bind to the MBD beads in a buffer, the buffer containing 100 mM-800 mM NaCl; and a non-ionic detergent. The target DNA and the non-target DNA preferably have a size in the range of 10-100 kb.

BRIEF DESCRIPTION OF THE DRAWINGS

FIG. 1 shows a schematic workflow for enrichment of target DNA in a mixture of target DNA (1) and non-target DNA (2) containing 5-methyl CpG (3). (1) and (2) are mixed with magnetic beads (4), which have been coated with protein A (7) to which methyl-binding domain (MBD2A) is fused to Fc (6) to form MBD2A-Fc beads in the presence of a non-ionic detergent (5). Eukaryotic genomic DNA (3) becomes bound to the MBD beads (4). A magnet (8) attracts the non-target DNA bound to the MBD beads leaving target DNA (1) in the supernatant.

FIG. 2 shows the effect of NaCl on MBD beads pull down of methylated DNA. The bands on the gel correspond to DNA in the supernatant after the DNA from Hela cells or *E. coli* cells is mixed with MBD beads. The results are shown at different salt concentrations increasing from 50 mM to 450 mM in 50 mM increments. Some Hela DNA was seen in the supernatant up to 200 mM NaCl.

FIG. 3 shows the results obtained on a 1% agarose gel of the pull down of methylated DNA by MBD beads. 500 ng of purified mammalian genomic DNA and 50 ng of tritiated *E. coli* DNA having a size of 10-20 kb were combined with varying amounts of MBD beads and the DNA recovered and analyzed on 1% agarose gels with SYBR® (Life Technologies, Carlsbad, Calif.) stain. Densitometry was used to determine the amount of mammalian DNA remaining in the supernatant after treatment with the varying concentrations of beads. The amount of E. coli DNA before and after mixing with beads was determined by scintillation counting.

Each sample was tested using no beads (c) or 20 µl or 40 µl (200 µg/ml) MBD beads. The genomic DNA from left to right starting in the top panel was purified from: Jurkat 2, HCT 116 1, HCT 116 2, IMR 90, 3T3 Mouse, Hela and Jurkat 1 cell lines. Effective removal of these DNAs was achieved with 20 µl of the MBD beads for IMR 90 cells and 40 µl of the MBD beads for the other cell types.

Greater than 92% of the mammalian genomic DNA in a single sample (with a mean of 97% for all samples tested) was removed by the MBD beads while at least 80% of E. coli DNA with a mean of 90% remained in the supernatant when compared with the starting amount.

FIG. 5 shows the results of SOLiD™ 4 sequencing of purified DNA from a human saliva sample (Life Technologies, Carlsbad, Calif.). In the absence of MBD beads, the input DNA sample showed that 96% of the DNA reads aligned to human, while only 4% of the DNA sequencing reads aligned to a mouth microbiome database (Human Oral Microbiome Database (HOMD) (www.HOMD.org)) (Chen et al., Database (Oxford). doi: 10.1093/database/baq013 (2010)). After enrichment with 20 µl MBD beads, the supernatant contained 10% of the DNA reads aligned to human and 90% of the sequence reads aligned to the HOMD. After treatment with 40 µl MBD beads, the supernatant contained 6.5% of the reads aligned to human DNA and 93.4% aligned to the HOMD.

FIGS. 6A and 6B show the improvement in efficiency in analyzing a microbiome from a human saliva sample using MBD beads to provide enrichment of the bacterial DNA by removal of the host DNA compared with the results obtained in the absence of MBD bead enrichment.

DETAILED DESCRIPTION OF THE
EMBODIMENTS

A "target" polynucleotide may refer to a polynucleotide having a particular desired feature where this feature may be a modification on a nucleoside in the polynucleotide. A "non-target" polynucleotide lacks this feature. This feature may render the polynucleotide capable of specific binding to an affinity domain immobilized on a solid support or matrix.

An example of target polynucleotides includes a mammalian genomic DNA that naturally contains a modified base, for example, methylated cytosine at a density of greater than 1/200 bases. An example of non-target polynucleotides includes a prokaryotic genomic DNA that does not contain the modified base or else contains the modified base at a density of less than 1/200 bases. In certain contexts, it may be desirable to efficiently obtain DNA having modified bases, where the modified bases occur at a density which enables this DNA to be enriched from a mixture of DNA including under-modified or unmodified DNA while in the other contexts, under-modified or unmodified DNA is of particular interest and may be preferentially recovered for further analysis.

A "modified" polynucleotide is a polynucleotide containing at least one specific base that differs from A, G, T or C by an addition of a side group such as a methyl group, hydroxymethyl, 5-formyl methyl, or carboxymethyl. Examples of modified bases include: 5-methylcytosine, N-6 methyladenine, and N-4 methylcytosine. The modified base can be further derivatized to include a tagging reagent, which could then be captured by an affinity agent. For example, 5-hmC could be glucosylated with a modified glucose, with the modified glucose containing biotin.

Present embodiments of the invention provide methods for separating a target polynucleotide from non-target polynucleotide. These methods achieve target polynucleotide enrichment by utilizing naturally occurring differences in the density of modified nucleotides in target DNA versus non-target DNA. For example, in order to sequence microbiome DNA (target DNA), it is desirable to remove contaminating mammalian genomic DNA (non-target DNA) from a DNA mixture obtained from a biological sample (such as human-derived saliva, mucosa, blood or tissue biopsies). The difference in density of modified bases in the microbiome DNA and the mammalian genomic DNA results in selective binding of the mammalian genomic DNA to an affinity matrix while the microbiome DNA remains in the supernatant.

This method provides a rapid single-step enrichment of target DNA that can be achieved within 15 minutes. This approach has the advantage of being rapid and avoiding further purification steps to remove non-specifically bound target DNA from the affinity matrix. The enriched DNA can then be sequenced using standard techniques and the microbial content rapidly determined (see FIG. 6A.)

Parameters that were found to play a role in rapid, selective and specific enrichment of target and non-target polynucleotides include one or more of the following:

(a) Protein-Coated Affinity-Binding Matrix for Binding Modified Polynucleotides

An "affinity matrix" as used herein refers to a matrix which is associated with an affinity protein or domain for binding polynucleotides containing modified bases. In an embodiment of the invention, a bead, more particularly, a magnetic bead, was used as an affinity matrix where the type of magnetic bead was, for example, a carboxylated polystyrene bead (for example a Seradyn, bead from Thermo Scientific, Waltham, Mass.) or a carboxylated polyvinyl chloride bead (for example, from Chemagen, PerkinElmer, Waltham, Mass.), more particularly a polystyrene bead. The examples illustrate the use of affinity protein-coated magnetic polystyrene bead where the magnetic polystyrene beads are available from New England Biolabs, Inc. (NEB), Ipswich, Mass.

The affinity protein or domain includes, for example, antibodies such as protein A, restriction endonucleases such as PvuRts1I or modifications thereof, a glucosyl transferase domain and/or modified nucleoside-binding domains or variants thereof such as methyl-binding domains. Examples of affinity proteins having binding specificity for CpG-methylated cytosine in DNA or RNA include MeCP2, MBD1, MBD2, MBD3, or MBD4 (U.S. Pat. No. 7,670,773). These share a 70-residue MBD (U.S. Patent Application Publication No. 2008/0260743). Any of these proteins or variants thereof may be used to coat the beads described above and are here referred to as MBD. Other molecules capable of binding methylated cytosine in DNA include ribozymes or other polynucleotides, proteins such as antibodies, UHRF1 (SRA domain, domains such as from human UHRF1) or murine NP95, CXXC1, DNMT1 proteins and modifications thereof or variants of restriction endonucleases that no longer have cleavage activity but retain their DNA binding specificity (see for example, Qian, *J. Biol. Chem.* 283:34490-34494 (2008); Voo, et al., *Mol Cell Biol.* 20(6):2108-2121 (2000); Pradhan, et al., *J. Biol. Chem.*, 274:33002-33010 (1999)).

The above proteins may be linked to a spacer to project the binding protein away from the surface of the bead by a desired distance, which is determined by the polymer length of the non-ionic detergent used in the sample buffer.

The examples describe the use of "MBD beads". These are magnetic beads coated with protein A to which is bound MBD2a-Fc in a ratio of two molecules of MBD2a-Fc to one molecule of protein A.

MBD2a-Fc has an amino acid sequence as follows:
Human MBD2 [AA 144-230]

(SEQ ID No. 1)
ESGKRMDCPALPPGWKKEEVIRKSGLSAGKSDVYYFSPSGKKFRSK

PQLARYLGNTVDLSSFDFRTGKMMPSKLQKNKQRLRNDPL.

Flexible Linker (SEQ ID No. 2)
AAADPIEGRGGGGG.

Human IgG1 [AA 99-330] Fc Region (SEQ ID No. 3)
DPKSSDKPHTCPPCPAPELLGGPSVFLFPPKPKDTLMISRTPEVTC

VVVDVSHEDPEVKFNWYVDGVEVHNAKTKPREEQYNSTYRVVSVLT

VLHQDWLNGKEYKCKVSNKALPAPIEKTISKAKGQPREPQVYTLPP

SRDELTKNQVSLTCLVKGFYPSDIAVEWESNGQPENNYKATPPVLD

SDGSFFLYSKLTVDKSRWQQGNVFSCSVMHEALHNHYTQKSLSLSP

GK.

Embodiments of the method utilize MBD beads to efficiently and rapidly separate DNA from prokaryotes that contain little or no methylated CpGs, compared to mammalian DNA which contains about 4% methylated cytosine adjacent to a guanine (mCpG).

(b) Salt in the Buffer

The amount of salt in the buffer containing the mixture of polynucleotides and the affinity-binding matrix was found to determine the density of methylated bases in polynucleotides capable of binding to the affinity matrix described above. Salts suitable for the purpose of enrichment include NaCl, KCl, or other salts in the range of 10 mM-800 mM. An example is 150-450 mM NaCl.

Figure 1:
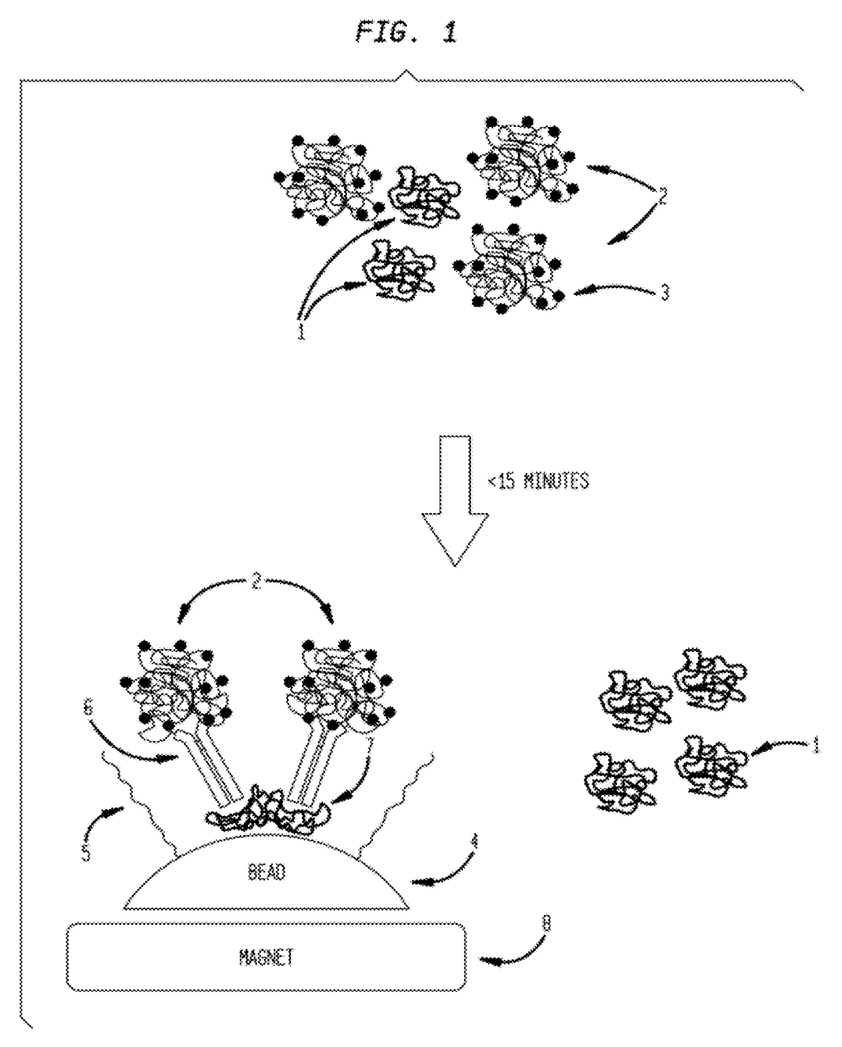
Figure 2:
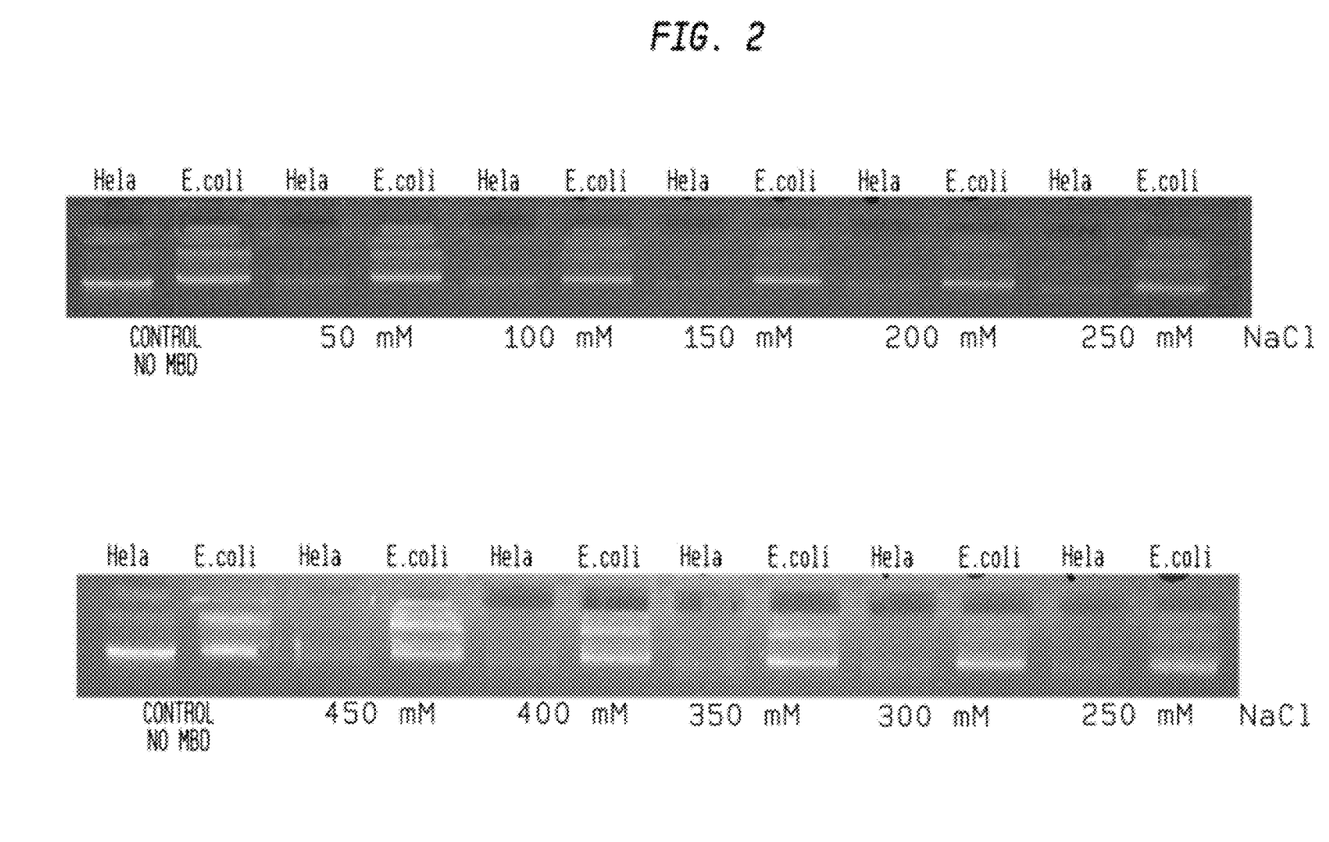
Figure 3:
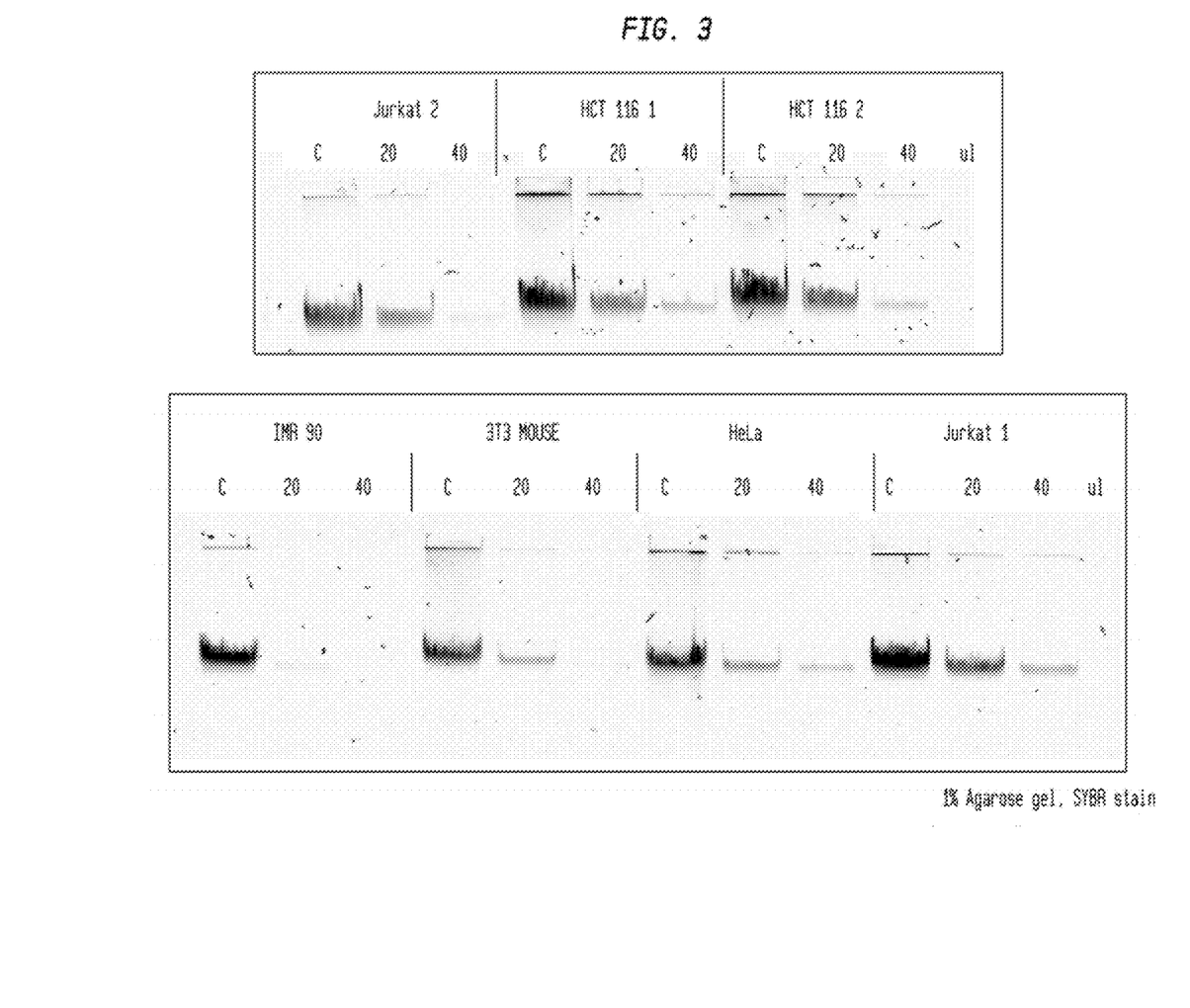
Figure 4:
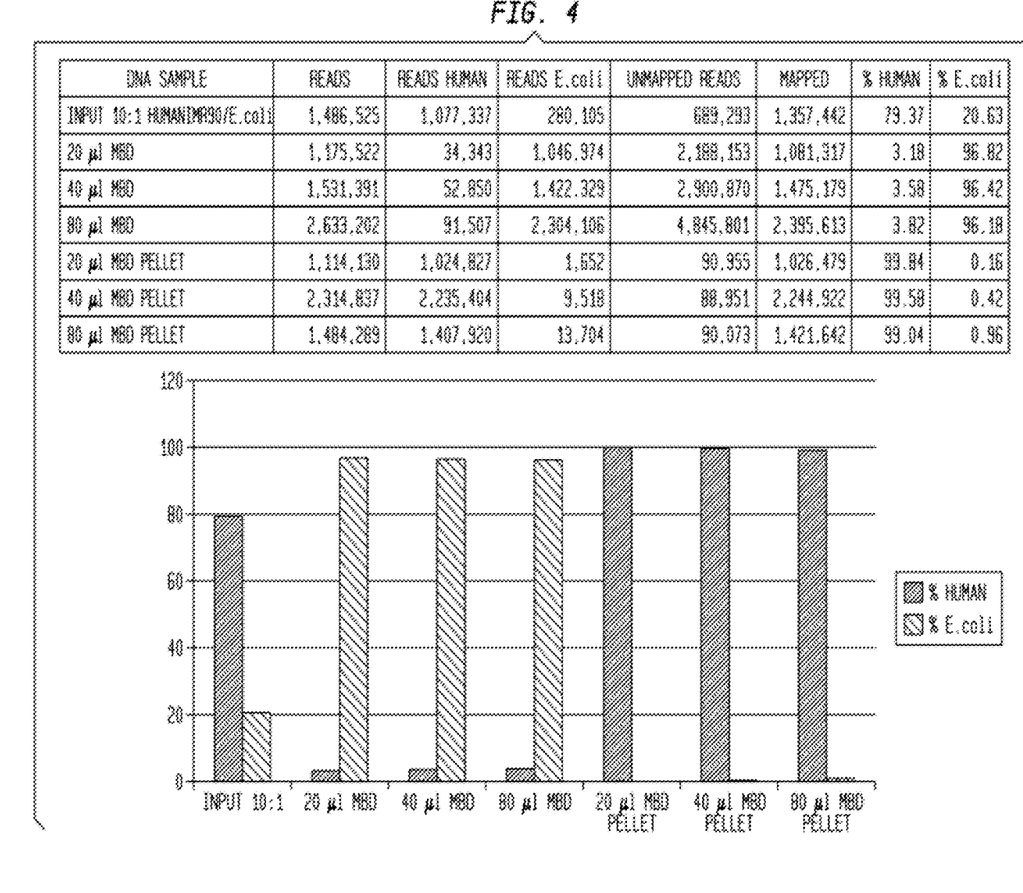
FIG. 4 shows the enrichment effect using different volumes of MBD beads (200 µg/ml) on a constant amount of human (IMR 90) and bacterial (E. coli) DNA (10:1) where the DNA fragments had a size of at least 20 kb. The supernatant was assayed on an Ion Torrent™ Personal Genome Machine (PGM)™ System (Life Technologies, Carlsbad, Calif.). The MBD bead-bound DNA was 99.5% human DNA as determined by aligned sequence reads while the aligned sequence reads of DNA in the supernatant was 96% E. coli. In the absence of MBD beads, the ratio of aligned sequence reads of human DNA to E. coli DNA was about 80% to about 20%.

Salt concentration can be varied as shown in FIG. 2 to determine the binding of polynucleotides containing a threshold amount of modified bases for the polynucleotides to bind to the affinity matrix. Here, the presence of salt exemplified by NaCl enhanced binding of modified DNA to the affinity matrix (MBD beads) resulting in the removal of host genomic DNA, as seen by the decrease in Hela DNA in the supernatant. For example, in the presence of 300 mM salt, only polynucleotide fragments with at least 3-fold to 6-fold more methylated CpGs than the unmodified DNA became bound to the affinity matrix. For human genomic polynucleotide fragments which are about 4% methylated, a 20 kb fragment would be expected to contain 800 methylated bases so that these polynucleotides readily bind to the affinity matrix in 300 mM salt. In contrast, polynucleotides that may have less than three methylated CpGs do not bind to the affinity matrix in this salt concentration.

(c) Non-Ionic Detergent

While not wishing to be limited by theory, it is here proposed that non-ionic detergents enhance the hydrophobicity of the affinity matrix to reduce non-specific binding of substantially unmethylated polynucleotides. One or more non-ionic polymeric detergents characterized by an uncharged hydrophilic head group such as Triton® X (Union Carbide Corp., Midland, Mich.), Brij® (Uniquema Americas LLC, Wilmington, Del.), Nonidet™ P-40 (Shell Brands International, Zug, Switzerland), or preferably Polysorbate (polyoxyethylene sorbitan monooleate) (Tween®, Uniqema Americas LLC, Wilmington, Del.) such as Tween 20, Tween 80, Tween 100 can be used at a concentration of less than 1%, more particularly at a concentration of less than 0.5%.

The use of non-ionic detergents and salt as described above resulted in a significant reduction in non-specific absorption of unmethylated CpG polynucleotides to MBD beads.

(d) Volume of Beads

The amount of beads that provides the desired effect of enrichment was tested in a suitable assay such as described in Example 3. It was shown in the example under the conditions described that 20 µl-40 µl of beads (4-8 µg of MBD2a-Fc loaded on 200 µg-400 µg protein A-coated magnetic beads) were optimal for binding 250 ng DNA.

(e) Size of Polynucleotides

Enrichment of target or non target polynucleotides is preferably achieved with large molecular weight polynucleotide molecules having a size in the range of about 10-100 kb, for example, polynucleotides having a size in the range of about 10 kb-20 kb. Methods of purifying DNA from cells prior to enrichment are known in the art. It is preferable to use methods that do not cause shear hence sonication or nebulization should be avoided. Instead, it is preferable to lyse the cells and use proteinase K followed by gentle organic extraction procedures (using chloroform and phenol (or ethanol) for phase separation and precipitation with ethanol) and/or a sizing column purification and/or agarose preparative gel electrophoresis (Sambrook, et al., *Molecular Cloning: A Laboratory Manual,* 3rd ed. pp. 6.4-6.12, Cold Spring Harbor Lab Press, Cold Spring Harbor, N.Y., (2001)).

All references cited herein, as well as U.S. Provisional Application Nos. 61/471,134 filed Apr. 2, 2011, 61/537,761 filed Sep. 22, 2011, 61/598,715 filed Feb. 14, 2012 and 61/599,253 filed Feb. 15, 2012, are hereby incorporated by reference.

EXAMPLES

Example 1

Adaptation of MBD Beads for Use in Enrichment of Unmodified DNA

MBD beads were obtained from NEB, Ipswich, Mass. (catalog #E2600).

The DNA was prepared by lysis of cells and chloroform-phenol extraction resulting in reduced DNA shear compared with sonication and provided fragments of at least 10-20 kb in length, preferably at least 20 kb.

Titration of salt concentration: 250 ng of input purified DNA (from HeLa or *E. coli*) was incubated with 40 µl of MBD beads in a buffer containing 10 mM Tris, pH 7.5, 1 mM EDTA, 1% Triton X100, 0.1% Tween 80 (Polysorbate 80, J.T. Baker, Phillipsburg, N.J.), and increasing concentrations of NaCl (50 mM to 450 mM). The samples were incubated at room temperature for ten minutes after which the MBD beads were separated from the rest of the sample in the presence of a magnet external to the reaction vessel. The supernatant from each sample was loaded on to a 1% agarose gel, and assayed by ethidium bromide staining. FIG. 2 shows that Hela DNA was effectively removed from the supernatant by MBD beads at all NaCl concentrations, while the *E. coli* DNA remained in the supernatant.

Volume of beads: 250 ng of various purified genomic DNAs from mammalian cell lines (Hela, Jurkat, HCT 116, 3T3) and a normal, non-cancer fetal lung fibroblast cell line (IMR 90) were incubated with 20 µl or 40 µl MBD beads or beads coated with protein A only. (20 µl MBD beads=4 µg MBD2a-Fc loaded on 200 µg protein A-coated magnetic beads, 40 µl MBD beads=8 µg MBD2a-Fc loaded on 400 µg Protein A-coated magnetic beads. (Stock Protein A magnetic beads (NEB) have a concentration of 10 mg/ml. Stock MDB2a-Fc have a concentration of 2 mg/ml (NEB).)

Samples were incubated for 15 minutes, the supernatants removed, loaded on a 1% agarose gel, and assayed by SYBR green DNA stain. Effective removal of the DNA from the supernatant was achieved when 40 µl of the MBD beads was used in the reaction. Effective removal of the IMR 90 DNA was seen at 20 µl of beads.

Example 2

Efficacy of Separation of Mammalian DNA from Prokaryotic DNA

A mixture of DNAs (about 250 ng total DNA) consisting of a 50:50 mixture of mammalian DNA (human Jurkat) and bacterial DNA (*E. coli* strain ER 1506) of at least 20 kb in length was added to 40 µl MBD beads (200 µg/ml) prepared as described above and incubated for about 10 minutes. The sample tube was then placed on a magnetic rack for 5 minutes to concentrate MBD beads bound to double-stranded CpG-methylated DNA.

The supernatant containing the prokaryotic, viral or metagenomic DNA was carefully removed, leaving behind the eukaryotic or human DNA which adhered to the MBD beads. This DNA was extracted from the MBD beads using heat and Tris buffer containing proteinase K. The supernatant DNA was analyzed on a 1% agarose gel.

Figure 5:
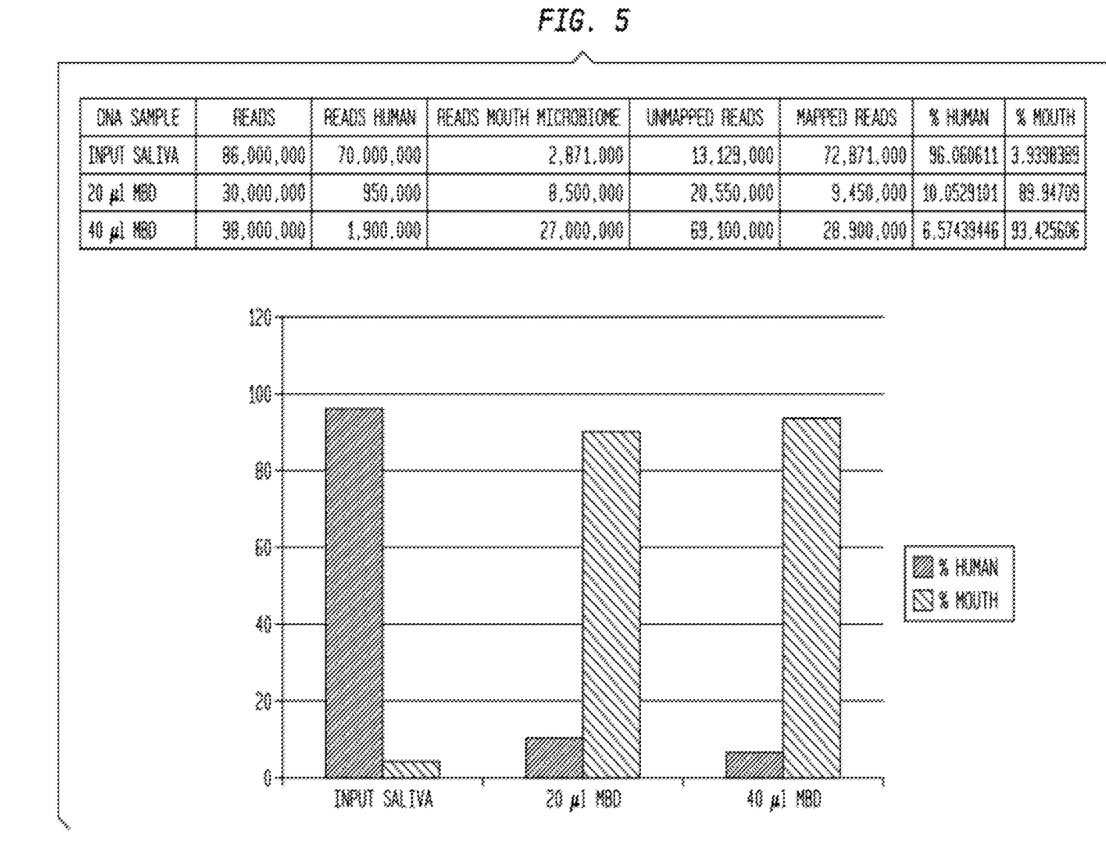

The band on the agarose gel corresponding to the 20 kb unbound *E. coli* DNA from the supernatant was further analyzed using an Ion Torrent PGM sequencer so as to analyze the DNA present (see FIG. 5).

It was found that at least 95% of the human DNA (CpG-methylated) remained bound to the magnetic bead matrix while the bacterial DNA, which was not CpG-methylated, remained in the supernatant with recovery rates of greater than 95%.

Example 3

Analysis of Human Saliva for Microbial Genomes

Any method for the purification of RNA-free and protein-free genomic DNA can be used such as, for example, proteinase K treatment followed by phenol/chloroform extraction and ethanol precipitation, lysozyme digestion, Qiagen (Valencia, Calif.) column preparation (for genomic DNA) or other methods. Sonication, nebulization, chaotropic salts, enzymatic treatment, rough handling, or any other procedure that would cause DNA shear were avoided as separation of microbial DNA from mammalian DNA is optimal when the fragments of DNA are greater in size than 10-20 KB and do not contain small molecular weight fragments (Sambrook, et al., *Molecular Cloning: A Laboratory Manual,* 3rd ed. pp. 6.4-6.12, Cold Spring Harbor Lab Press, Cold Spring Harbor, N.Y., (2001)). The DNA quality and quantity extracted from saliva can be determined by agarose gel electrophoresis of the sample alongside a DNA marker (2-log DNA ladder, NEB# N3200S, Ipswich, Mass.).

In this example, normal human saliva was acquired from Innovative Research (Novi, Mich.). 250 ml of saliva was added to 10 µl 1M Tris-HCL pH. 7.5, 5 µl 500 mM EDTA, 5 µl 20% SDS, 3 µl 20 mg/ml proteinase K (NEB# P8102S, Ipswich, Mass.), and incubated at 50° C. for 2 hours and ethanol-extracted. The pellet was air-dried, suspended in 25 mls of buffer (10 mM Tris, 1 mM EDTA, 100 µl RNaseA (10 mg)) and incubated at 37° C. for 1 hour. The released product was extracted with Tris-EDTA equilibrated phenol, once with dichloromethane, and 2 volumes ethanol (ETOH) were added. The product was then spun and the pellet air-dried as before and resuspended in 250 µl TE to give a final concentration of 150 µg/ml, 37.5 µg total.

Agarose gel analysis revealed ~50% of DNA was degraded below 10 kb. To further purify the DNA and enrich for high molecular weight fragments, the sample was loaded on a 1% low melt agarose gel plus 1× SYBR Safe DNA Gel Stain (Life Technologies, Carlsbad, Calif.). The large ~10-15 kb band was cut out of the gel, heated to 50° C., and 10 units Beta Agarase I (NEB #M0392S, Ipswich, Mass.), plus 100 µl 10× reaction buffer, in a total volume of 1 ml, was added to the sample and incubated at 42° C., for 30 minutes. 2 volumes of ETOH was added to the sample, spun, dried, and suspended in TE as above.

The above procedure was repeated on a second 250 ml pooled saliva sample of the same lot number and the two purified DNA samples were combined and the DNA concentration adjusted to 70 µg/ml; total yield was 40 µg.

The purified human saliva DNA described above was mixed with MBD beads in the following ratio: 250 ng DNA to 20 µl of MBD beads, or 40 µl MBD beads. Without the use of MBD beads to enrich for prokaryotic DNA, the DNA sample showed that 96% of the DNA reads aligned to human, while only 4% of the DNA sequencing reads aligned to HOMD.

Figure 6A:
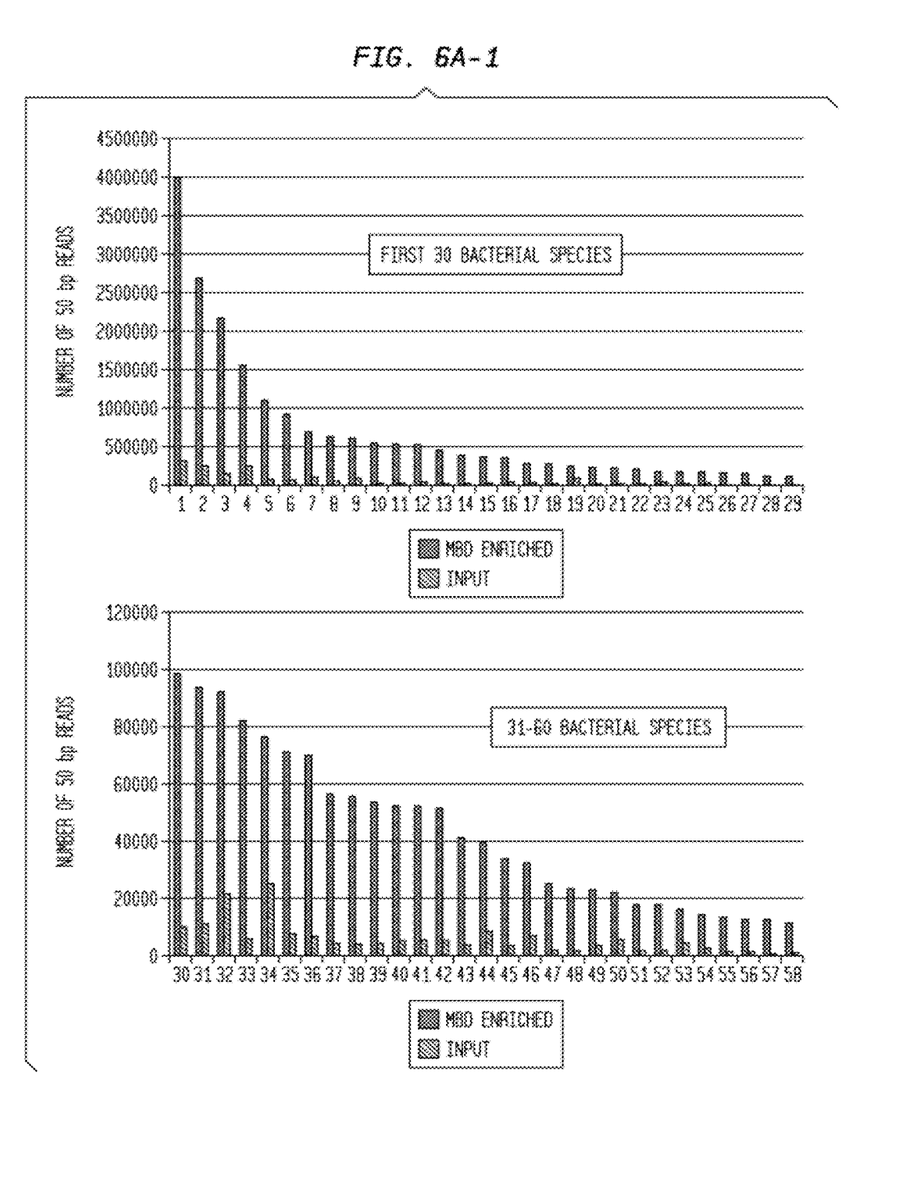
FIG. 6A shows sequencing reads mapped to 150 known oral microbes (numbered 1-150 on the x-axis) before and after enrichment. The reads were aligned to 150 different bacterial species specified in the HOMD using Bowtie 0.12 alignment software (Langmead et al. Genome Biology 10: R25 (2009). doi:10.1186/gb-2009-10-3-r25). Overall, the number of aligned reads from the enriched sample increased 10-fold, with no loss of species diversity.
FIG. 6B provides the bacterial species corresponding to the numbers on the X-axis of the graph in FIG. 6A.
Figure 6A:
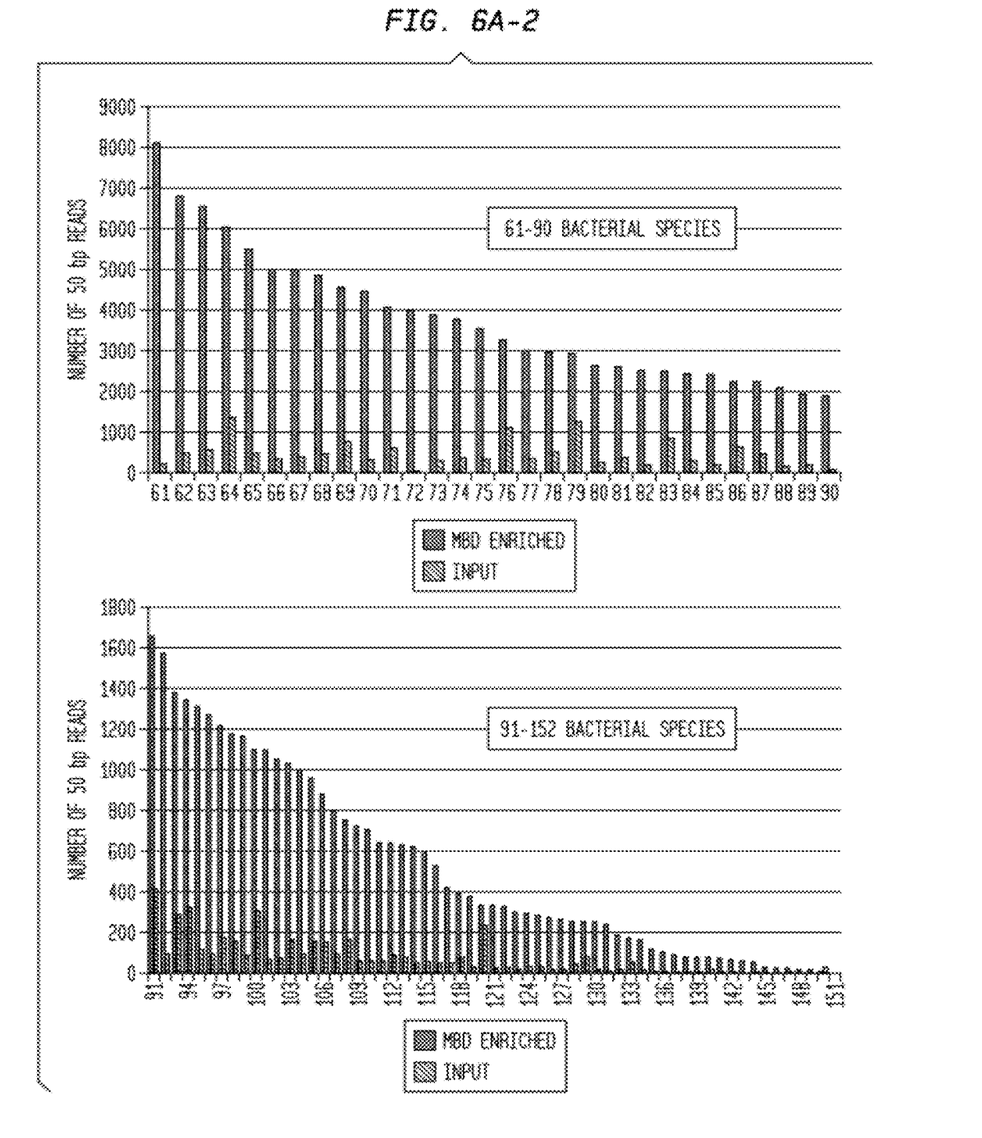
Figure 6B:
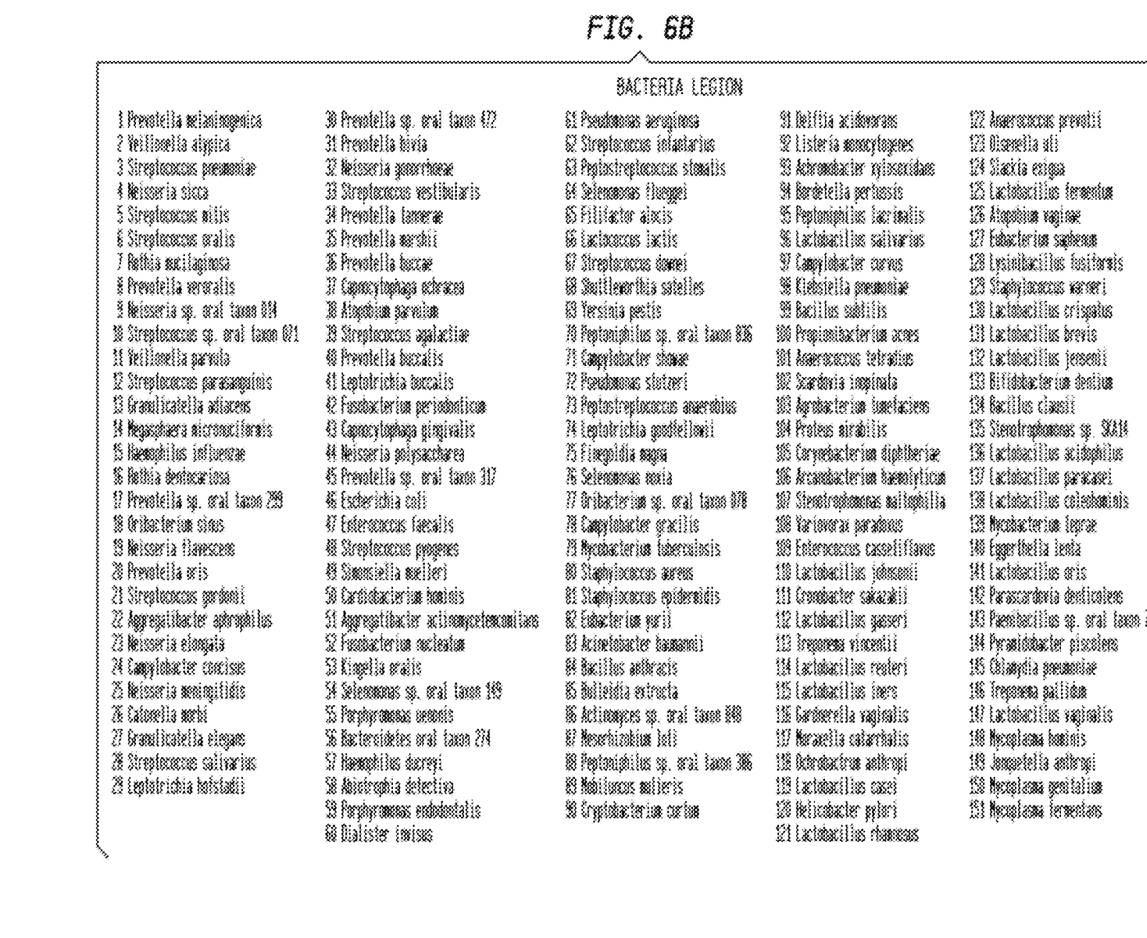

After enrichment with 20 µl MBD beads, 10% of the DNA reads aligned to human, and 90% of the reads aligned to HOMD. After treatment with 40 µl MBD beads, 6.5% of the reads aligned to human, and 93.4% aligned to HOMD (FIG. 6A).

Example 4

Enrichment of Human Mitochondrial DNA

Human mitochondrial DNA is a circular DNA molecule of about 16.5 kb. It encodes 37 genes: 13 for subunits of respiratory complexes I, III, IV and V, 22 for mitochondrial tRNA (for the 20 standard amino acids, plus an extra gene for leucine and serine), and 2 for rRNA. One mitochondrion can contain two to ten copies of its DNA (Chan, *Cell*, 125 (7): 1241-1252 (2006). doi:10.1016/j.cell.2006.06.010.)). Many diseases are associated with mitochondrial DNA defects and so it is desirable to enrich for mitochondrial DNA. Using the methods described herein, two input samples (4.75×105 bases) were compared with four enriched supernatant samples (1.6×105 bases) and two pellet samples (1.5×106 bases) using IMR 90 DNA assayed on an Ion Torrent PGM System. All base reads were aligned to the human genome (hg19) using Bowtie 0.12 alignment software and a chromosome distribution was performed. It was found that the MBD supernatant sample had a 160-fold enrichment of mitochondrial DNA as compared to the input sample. Conversely, the pellet contained no detectable mitochondrial DNA.

---

What is claimed is:

1. A composition, comprising:
   (a) a mixture comprising polynucleotides from one or more bacteria and polynucleotides from a methylated genome, the polynucleotides in the mixture having a median size in the range of 10-100 Kb;
   (b) an affinity matrix comprising a protein or a polypeptide domain that is capable of selectively binding to methylated polynucleotides but not non-methylated polynucleotides; and
   (c) a buffer containing effective amounts of a salt and a non-ionic detergent.

2. A composition, according to claim 1, wherein the effective amount of salt is 10 mM-800 mM.

3. A composition according to claim 1, wherein the methylated bases in the methylated genome occur at a frequency of at least 1 modified base in 200 bases.

4. A method for enriching polynucleotides from a mixture, comprising:
   (a) combining: (i) a mixture comprising non-methylated polynucleotides from one or more bacteria and polynucleotides from a methylated genome, the polynucleotides in the mixture having a median size in the range of 10-100 Kb, with (ii) a buffer containing effective amounts of a salt and a non-ionic detergent and (iii) an affinity matrix comprising a protein or a polypeptide domain that is capable of selectively binding to methylated polynucleotides but not non-methylated polynucleotides;
   (b) permitting binding of the methylated polynucleotides to the affinity matrix;
   (c) collecting the unbound polynucleotides, thereby obtaining an enriched preparation of non-methylated polynucleotides; and
   (d) analyzing the enriched preparation of non-methylated polynucleotides.

5. A method according to claim 4, wherein the methylated polynucleotides that are bound to the affinity matrix are at least 90% of the polynucleotides in the mixture prior to enrichment.

6. A method according to claim 4, wherein the non-methylated polynucleotides in the unbound fraction comprise no more than 10% of the polynucleotides in the mixture prior to enrichment.

7. A method according to claim 4, wherein the methylated genome comprises methylated cytosines.

8. A method according to claim 4, wherein the mixture of polynucleotides prior to enrichment is obtained from a biological sample and comprises prokaryotic and mammalian genomic DNA wherein the mixture comprises at least 50% mammalian genomic DNA.

9. A method according to claim 4, wherein the analyzing is done by sequencing, cloning or amplification to determine a genomic identity for the non-target polynucleotides.

10. A method according to claim 4, wherein the affinity matrix comprises a methyl-binding domain (MBD) selected from the group consisting of UHRF1(SRA), CXX1, DNMT1, MBD and methyl-binding variants thereof.

11. A method according to claim 4, wherein the affinity matrix comprises magnetic beads.

12. A method according to claim 11, wherein the magnetic beads are coated with protein A bound to MBD2a-Fcbu.

13. A method according to claim 4, wherein the salt is NaCl in a concentration range of 10 mM-800 mM.

14. A method of enhancing separation of polynucleotides of a non-methylated genome from polynucleotides of a methylated genome, comprising:
  (a) providing a composition according to claim 1;
  (b) permitting the methylated polynucleotides to bind to the affinity matrix to form a product that is immobilized on the matrix; and
  (c) performing amplification and/or sequencing of at least one of the bound polynucleotide or the unbound polynucleotide.

15. A method according to claim 14, wherein the mixture of methylated and unmethylated polynucleotides comprise fragments from one or more bacterial genomes and one or more mammalian genomes.

16. A method according to claim 14, wherein the matrix is a magnetic bead.

17. A method according to claim 14, wherein the affinity matrix comprises a methyl-binding domain (MBD) selected from the group consisting of—UHRF1(SRA), CXX1, DNMT1, MBD and methyl-binding variants thereof.

18. A method according to claim 14, wherein the effective amount of salt is in the range of 100 mM-800 mM NaCl.

19. The composition of claim 1, wherein the polynucleotides from a non-methylated genome are fragments of bacterial genomic DNA and the polynucleotides from a methylated genome are fragments of mammalian genomic DNA.

20. The method of claim 4, wherein the polynucleotides from a non-methylated genome are fragments of bacterial genomic DNA and the polynucleotides from a methylated genome are fragments of mammalian genomic DNA.

* * * * *

SEQUENCE LISTING

```
<160> NUMBER OF SEQ ID NOS: 3

<210> SEQ ID NO 1
<211> LENGTH: 86
<212> TYPE: PRT
<213> ORGANISM: human
<220> FEATURE:
<221> NAME/KEY: MISC_FEATURE
<222> LOCATION: (1)..(86)
<223> OTHER INFORMATION: 1-86 amino acid residues correspond to 144-230
      in Human MBD2

<400> SEQUENCE: 1

Glu Ser Gly Lys Arg Met Asp Cys Pro Ala Leu Pro Pro Gly Trp Lys
1               5                   10                  15

Lys Glu Glu Val Ile Arg Lys Ser Gly Leu Ser Ala Gly Lys Ser Asp
                20                  25                  30

Val Tyr Tyr Phe Ser Pro Ser Gly Lys Lys Phe Arg Ser Lys Pro Gln
            35                  40                  45

Leu Ala Arg Tyr Leu Gly Asn Thr Val Asp Leu Ser Ser Phe Asp Phe
    50                  55                  60

Arg Thr Gly Lys Met Met Pro Ser Lys Leu Gln Lys Asn Lys Gln Arg
65                  70                  75                  80

Leu Arg Asn Asp Pro Leu
                85

<210> SEQ ID NO 2
<211> LENGTH: 14
<212> TYPE: PRT
<213> ORGANISM: artificial sequence
<220> FEATURE:
<223> OTHER INFORMATION: flexible linker

<400> SEQUENCE: 2

Ala Ala Ala Asp Pro Ile Glu Gly Arg Gly Gly Gly Gly Gly
1               5                   10

<210> SEQ ID NO 3
<211> LENGTH: 232
<212> TYPE: PRT
<213> ORGANISM: human
<220> FEATURE:
<221> NAME/KEY: MISC_FEATURE
<222> LOCATION: (1)..(232)
<223> OTHER INFORMATION: Amino acid residues 1-232 correspond to the Fc
      region (residues 99-330) of the human IgG1

<400> SEQUENCE: 3

Asp Pro Lys Ser Ser Asp Lys Pro His Thr Cys Pro Pro Cys Pro Ala
1               5                   10                  15

Pro Glu Leu Leu Gly Gly Pro Ser Val Phe Leu Phe Pro Pro Lys Pro
```

-continued

```
               20                  25                  30
Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
            85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
        130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Ala Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
        210                 215                 220

Ser Leu Ser Leu Ser Pro Gly Lys
225                 230
```